(12) United States Patent
Ryabov et al.

(10) Patent No.: US 9,095,285 B2
(45) Date of Patent: Aug. 4, 2015

(54) PORTABLE BIOMETRIC IDENTIFICATION DEVICE USING A DORSAL HAND VEIN PATTERN

(71) Applicants: Yaroslav Ryabov, Rockville, MD (US); Denis Broydo, Rockville, MD (US)

(72) Inventors: Yaroslav Ryabov, Rockville, MD (US); Denis Broydo, Rockville, MD (US)

(*) Notice: Subject to any disclaimer, the term of this patent is extended or adjusted under 35 U.S.C. 154(b) by 320 days.

(21) Appl. No.: 13/860,669

(22) Filed: Apr. 11, 2013

(65) Prior Publication Data

US 2014/0307074 A1    Oct. 16, 2014

(51) Int. Cl.
*A61B 5/117*    (2006.01)
*H04N 5/33*    (2006.01)
*A61B 5/00*    (2006.01)
*G06K 9/00*    (2006.01)

(52) U.S. Cl.
CPC    *A61B 5/117* (2013.01); *H04N 5/33* (2013.01); *A61B 5/0077* (2013.01); *A61B 5/489* (2013.01); *A61B 5/6825* (2013.01); *A61B 5/6898* (2013.01); *G06K 9/00* (2013.01)

(58) Field of Classification Search
CPC ............. A61B 5/117; H04N 5/33; G06K 9/00
USPC ........ 348/77, 61, 78, 180, 189; 382/117, 115, 382/116, 124, 118; 726/2
See application file for complete search history.

(56) References Cited

U.S. PATENT DOCUMENTS 8,811,681 B2 *    8/2014    Watanabe ..................... 382/115
2012/0281890 A1 *    11/2012    Kamakura et al. ............ 382/126

* cited by examiner

*Primary Examiner* — Jefferey Harold
*Assistant Examiner* — Jean W Desir
(74) *Attorney, Agent, or Firm* — Nadya Reingand

(57) ABSTRACT

A portable device for personal identification using a dorsal hand vein-pattern in preferable configuration is disclosed. The mobile device utilizes an on-board camera operating in both visible and near infrared range, a memory unit, a processor and Speeded-Up Robust Features algorithm for image acquisition, processing and comparison against the existing database of hand vein-pattern images. The matching criterion between the images to be used for the person's authentication. Device can optionally use wireless connection for image transferring and processing.

20 Claims, 7 Drawing Sheets

A.                                                                   B.

A.

B.

PORTABLE BIOMETRIC IDENTIFICATION DEVICE USING A DORSAL HAND VEIN PATTERN

FIELD OF INVENTION

The present invention relates broadly to device for biometric person identification based on the platform of a Portable Assistance Device (PAD) such a smartphone, cell phone or tablet.

More precisely, the invention is based on the analysis and comparison of unique vein-patterns of human hands. The technology can be applied to various human populations, regardless of race, skin color or age (i.e. newborns, toddlers, teenagers, adults, and elderly people).

BACKGROUND OF THE INVENTION

The progress of the information age brings unprecedented changes to the human society. The requirements related the personal information are being growing dramatically day by clay. As the result, the personal identification, protection and security become extremely important in the modern age.

There are various methods of personal and/or biometric identification have been developed, including fingerprinting, face-voice-recognition, vein pattern (iris, palm), etc.

There are multiple problems associated with the existing methods, such as requirement for in-contact authentication procedure, time-consuming or obstructive procedure, unreliable measurements and low recognition rate.

For example, the accuracy of a face-recognition-based personal identification is relatively low as the technology has to overcome the problems of lighting, pose, orientation and gesture. Fingerprint identification is widely used for personal identification. However, it is difficult to acquire fingerprint features (i.e. minutiae), for some people such as elderly people, manual laborers, etc. Moreover, in-contact identification devices may invoke hygiene concern and reluctance to use by a general public. As a result, other biometric characteristics are receiving increasing attention.

Recently, a growing trend towards relieving the users from a contact device has emerged and the idea of peg-free, or further contact-free, hand biometrics have been is proposed. The hand vein recognition technology has been also proposed for image biometrical verification, see, for example U.S. Pat. No. 4,699,149 by Rice, US20120281890 by Kamakura and U.S. Pat. No. 5,787,185 by Clayden.

Compared to other biometric authentication techniques, the vein recognition has many advantages, such as uniqueness, life-long, time invariant consistency of the vein-pattern for each human body, as well as a non-contact, fast, unobtrusive vein-pattern image acquisition procedure.

FIG. 1 shows the typical example of matched portions of the two superimposed vein-patterns of a person, as shown in U.S. Pat. No. 5,787,185 by Clayden.

The advancement in biometric image matching technology has promoted the development of various biometric identification systems.

Vein biometric systems are also capable to record the infrared absorption patterns to produce unique and private identification templates for users, see, for example U.S. Pat. No. 8,229,178 by Zhang.

The matching and comparison of images is part of many modern computer-vision applications. Image registration, camera calibration, object recognition, and image retrieval, to mention a few, see for example U.S. Pat. No. 8,165,401 by Funayama.

The contemporary compact devices such as a smartphone are capable of performing the task of finding correspondences between two images. Moreover, the smartphone can be modified to process the image at the infrared part of the spectrum with minimal or no modification.

The disclosed invention provides a novel, compact, fast, portable and mobile authentication and identification device of a person biased on person's hand vein-pattern.

The preferred embodiment of the invention uses an image of the vein-pattern of a dorsal (back) side of a human palm for biometric authentication of a person. There is no limitation, however, to apply the disclosed method to the front side of human palm, as well as to other regions of skin of human body, as long as blood vessels are located relatively close to the skin surface.

The surface of the person's hand dorsal side is less susceptible to accidental damage, thus making disclose device preferable for the situations of field deployment. Moreover, it is much more convenient to acquire the images of the hand dorsal side of small children and newborns.

Furthermore, for small children it might be preferable to use the images of their feet particularly in infrared spectrum.

The disclosed device and technology is relies on the discovering intrinsically specific points of interest and match them using geometric affine, projective, or other types of geometric transformations.

The disclosed device and technology is relies on the image processing algorithm similar to Speeded-Up Robust Features (SURF) algorithm reported by Bay et. al. in "Surf: Speeded up robust features", ECCV (European Conference on Computer Vision), 2006, pp. 404-417.

Together with this algorithm the disclosed device employs geometric affine and projective transformations which are insensitive to rotations, scaling, tilt, image plane, etc., making the disclosed our technology applicable to biometric identification of humans of all ages: from newborns to adults.

The term "vein-pattern", as used herein is defined as the image having a pattern of veins, capillaries and other blood vessels that are unique for each individual.

The term "PAD", as used herein is defined as any mobile Portable Assistance Device, such as a cell phone, a smartphone, a tablet computer, a personal computer, etc.

The term "identification", as used herein is defined as a procedure of providing and proving an identity of the individual by searching against a database of previously acquired information.

The term "NIR", as used herein is defined as electromagnetic radiation within the 750 mm-2500 nm range of the spectrum.

The term "point of interest" of an image, as used herein is defined as a pixel of the image with a specific coordinates on the image. The local image features around of the point of interest are stable under local and global image perturbations, such as deformations as those arising from perspective transformations (e.g. affine transformations, scale changes, rotations and/or translations) as well as illumination/brightness variations, such that the locations of the points of interest can be reliably computed with a high degree of reproducibility.

The term "descriptor" of a point of interest, as used here is defined as a set of numeric values, usually represented by a 64-dimentional vector, which contains information about the local environment of the point of interest.

In the general embodiment of the invention, the image acquisition is performed using a PAD. In such embodiment the PAD-connected camera is used to obtain the images of blood veins. The camera can be either a PAD built-in camera or connected to the PAD by a wire or wirelessly.

In other embodiment of the invention the disclosed personal authentication device includes a switching capabilities between visible and near infrared spectral ranges, namely, acquiring the vein-patter image from a person under the visible and the near infrared spectrum and subsequent extracting points of interest, their locations and descriptors, from the acquired images.

In another embodiment of invention a lighting feature is provided by the device to improve the quality of the image both in the visible and the near infrared spectral regions.

The disclosed device for non-contact person authentication and identification do not require a direct contact between the disclosed biometric device and a human subject, making it indispensible tool for sterile hospital environment when the alleviation of possible contamination is important.

Being portable, the disclosed invention can provide an immediate personnel identification or authorization at virtually any location. The invention might also be important for the personal working in remote areas or in the areas with underdeveloped/damaged infrastructure.

The disclosed invention can also find a particular application in instances where the restricted authorized access is required, such as admission to secure sites, operation of sensitive machinery or credit/cash dispensing.

It is also possible to use the disclosed invention for statistical data analysis and medical diagnostics.

Moreover, the disclosed invention can be used for indication of subcutaneous bleeding, new born birth trauma, arthritis, symptoms of a high blood pressure and atherosclerosis, etc.

Further features and aspects of the present invention will become apparent from the following description of preferred and optional embodiments with reference to the attached drawings.

SUMMARY OF THE INVENTION

A portable identification device using an individual hand vein-pattern is disclosed. The device is based on a smartphone with a built-in camera to acquire a near-infrared image of a skin area with the vein-pattern of the individual.

A smartphone performs a processing of the acquired image to extract a vein-pattern image and applies a Speeded-Up Robust Features (SURF) method (with adjustable hessian thresholds to deduct of points of interest from the image and create a 64-dimensional descriptor vector for the pixel's neighborhood for each of the point of interest. In order to facilitate the vein-pattern extraction, a spatial low- and high-frequency filtering is applied to the (optionally gray-scale) vein-pattern image, along with a contrast enhancement. A smartphone compares the descriptors of the acquired image and an image stored in a database and further uses a minimum (Euclidian) distance criterion between descriptor to establish pairs of matching points of interest for two images, resulting in an individual identification based on a threshold value.

The invention uses an adjustable threshold value of minimum distance between descriptor vectors. It also uses an adjustable number of matching points of interest that determine the possible identification. The device can include additional processing to improve an accuracy of the identification by calculating a transformation matrix using the coordinates of the matched pairs and calculating transformed coordinates of the points of interest of the input image. The transformed coordinates can be compared with initial coordinates for improved individual identification using a cumulative threshold (a mean square distance) for distance between the initial and the transformed coordinates. The transformation matrix can belong to affine or projective transformation class.

The device can use a smartphone memory, a 3G or 4G technology, Bluetooth, or Wi-Fi to access the database. Moreover, the camera of the device can have auto-focus feature and being switched to operate in visible or NIR spectrum regions. A lighting feature is provided by the device to improve the quality of the image both in the visible and the NIR light. The smartphone can employ a wireless communication with a remote server for storage, image processing and exchanging the identification information. Apart of the personal identification, disclosed device is capable of collecting the personal biometric information, accessing the individually specific information for the identified person and/or granting an individual access to the specific information or site. The device is also capable of performing tasks of personnel/population surveying and management.

BRIEF DESCRIPTION OF THE DRAWINGS

FIG. 6A illustrates a good match between the points of interest while FIG. 6B illustrates a bad match.

DETAILED DESCRIPTION OF THE PREFERRED EMBODIMENT

Figure 1:
FIG. 1: Prior Art. The matched portions of the two superimposed patterns.
Figure 2:
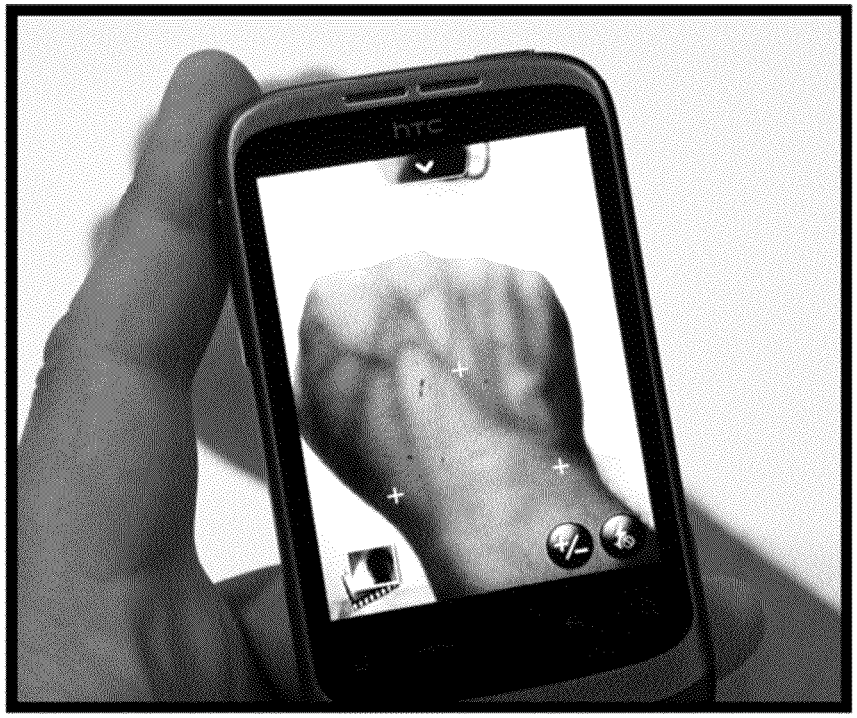
FIG. 2: The general layout of the proposed invention.

The disclosed invention is based on a device and method for biometric human identification based on the platform of a PAD. The general layout of the disclosed invention is show in FIG. 2.

In the preferred embodiment of the invention, the image acquisition is performed using a smartphone. In such embodiment a smartphone-built-in (standard) camera is used to obtain the blood vein-pattern.

In preferable embodiment of the invention the distance from the camera and the object (i.e. a skin area) is within 0.1-1 meter range.

In another embodiment of the invention, the camera is specifically modified to adjust the camera sensitivity for different wavelength regions, i.e. spectral region or spectrum.

In the preferred embodiment of the invention, the Near Infra Red (NIR) region of electromagnetic spectrum, such as a wavelength region between 750 nm and 2500 nm, for example, is used by the camera. This embodiment exploits the fact that oxygenated blood in vein vessels absorbs the NIR part of the spectrum more efficiently than the visible spectrum, while the outer skin layers are sufficiently transparent for the NIR radiation.

In yet another embodiment of the invention, a specific camera modification is implemented that enables a sequential operation within two spectral regions, for example, between visible and NIR regions, preferably having an engaging/disengaging mechanism (e.g. a button).

In yet another embodiment of the invention, the built-in NIR illumination device is used in combination with the PDA if necessary to improve the image acquisition by the camera at low-light conditions, preferably having an engaging/disengaging mechanism (e.g. a button).

The disclosed invention is based on the device and method to compare and match the unique vein patterns of human hands. The method includes an algorithm capable of processing and comparing the captured image against the set of images stored in the database.

The database can be located either within the PAD memory unit or remotely. For the latter case, the PAD is capable of a bi-directional remote access, including a real-time access, to the database using any wireless protocol available (e.g. Wi-Fi or Bluetooth).

In the preferred embodiment, of the invention all the elements of the image processing and algorithm operation are realized on the platform of onboard PAD processing unit, such as a smartphone CPU. It is also possible, however, to implement a remote processing (e.g. remote server) for the algorithm operation, either entirely or partially.

In the preferred embodiment of the invention, the algorithm is capable of saving captured images in the database and processing any stored images within the database, e.g. performing a search and statistical data analysis upon the stored images within the database.

Figure 3:
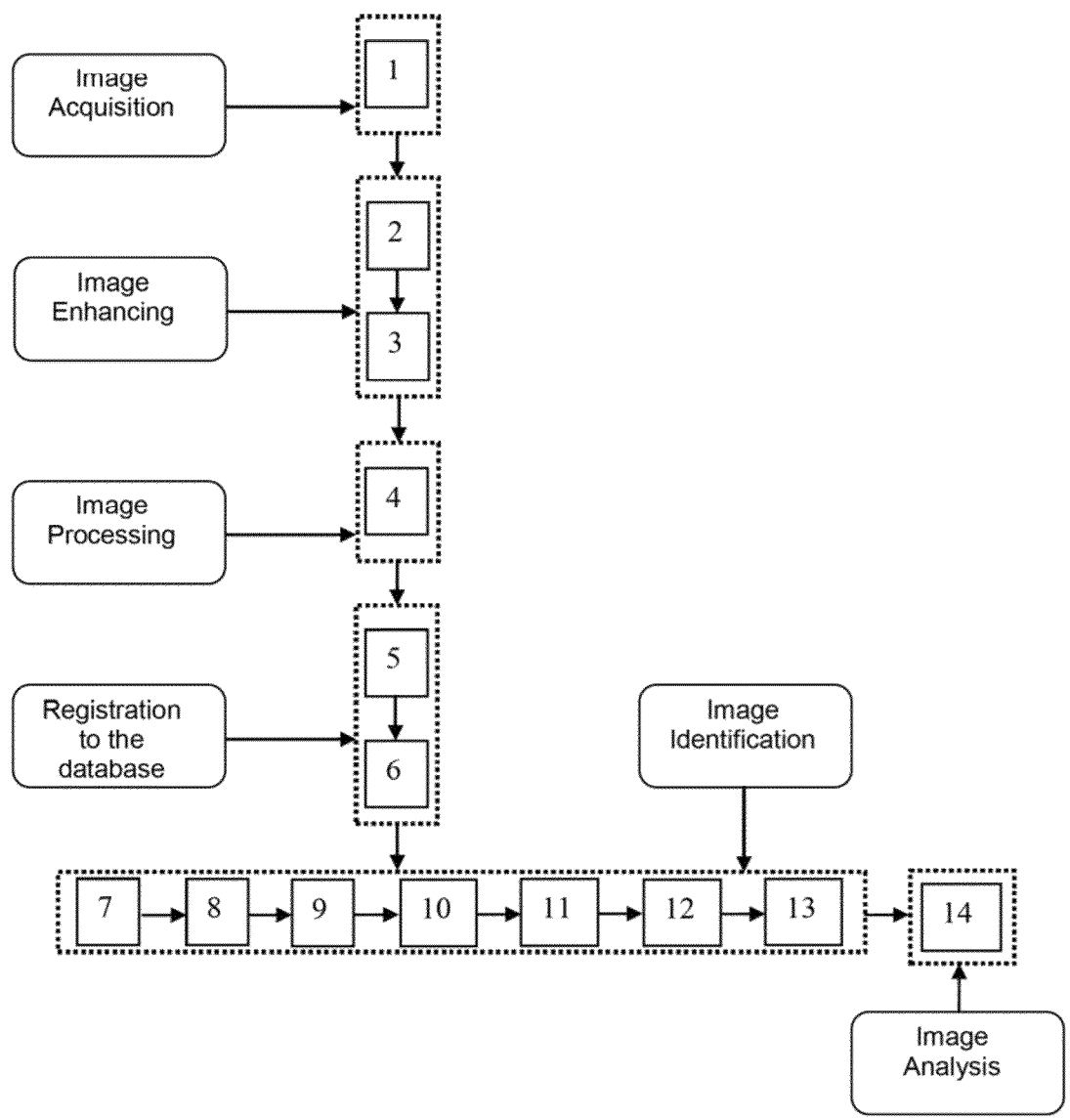
FIG. 3: The block-diagram of the image matching algorithm disclosed in the preferred embodiment invention.

FIG. 3 shows the block-diagram of the image matching algorithm disclosed in the preferred embodiment of the invention. The numbering in FIG. 3 corresponds to the software routine steps that are used in the preferred embodiment of the disclosed biometric identification device.

The realization of the identification routine in the preferred embodiment of the invention is described in details below and comprises the following steps:

Image Acquisition:
Step-1: An input image acquisition of human dorsal hand with PAD camera, selecting the area of interest from the raw image.

Image Enhancing:
Step-2: Enhancing the input image, using: i) Conversion the input image to a gray-scale image (i.e. intensity image); ii) Enhancing contrast of the gray-scale image by mapping the existing intensity range of the gray-scale image to the entire possible intensity range and leaving out an adjustable percentage of pixels (e.g. one percent of pixels) having lowest and highest intensities.

Step-3: Further enhancing the contrast of the input image by application of a high-frequency and a low-frequency image filtering with respective adjustable parameters. Obtaining the image of a hand vein pattern image from the enhanced image.

Image Processing:
Step-4: Application of the SURF algorithm to the (hand) vein pattern to obtain locations of points of interest of the vein pattern; the SURF algorithm using a set of adjustable parameters, including hessian threshold values, hessian balance value, and number hessian octaves. Preparing a unique descriptor for each of the points of interest. Each descriptor includes a 64-dimentional vector which, in turn, contains the information about local pixel neighborhood of such respective point of interest.

Registration to Database:
Step-5: Storing to data base the original image, its enhanced image, locations of the points of interest, descriptors, personal information about the individual being imaged, a geo-location information (e.g. GPS coordinates), time, etc.

Step-6: Choosing a database image from the multiple images in the database; the database image including its enhanced image, locations of points of interest, the descriptors, a personal information about the individual being imaged a geo-location information (e.g. GPS coordinates), time, etc.

In the preferred embodiment of the invention the linear search over the database of previously collected images is employed. Alternative search techniques can be used, such as a decision-tree clustering at the particular point of interest. The binary or, more general K-tree-structures at the space of the chosen descriptor can be used to provide a non-linear search time reduction.

Image Identification:
Step-7: Comparing the set of descriptors (Step-4) with the descriptors retrieved from the database image (Step-7). Calculation the Euclidian distance between descriptors in a 64-dimensional space of the descriptor vectors. Recording the measured distance for the respective pair of descriptors.

Figure 5:
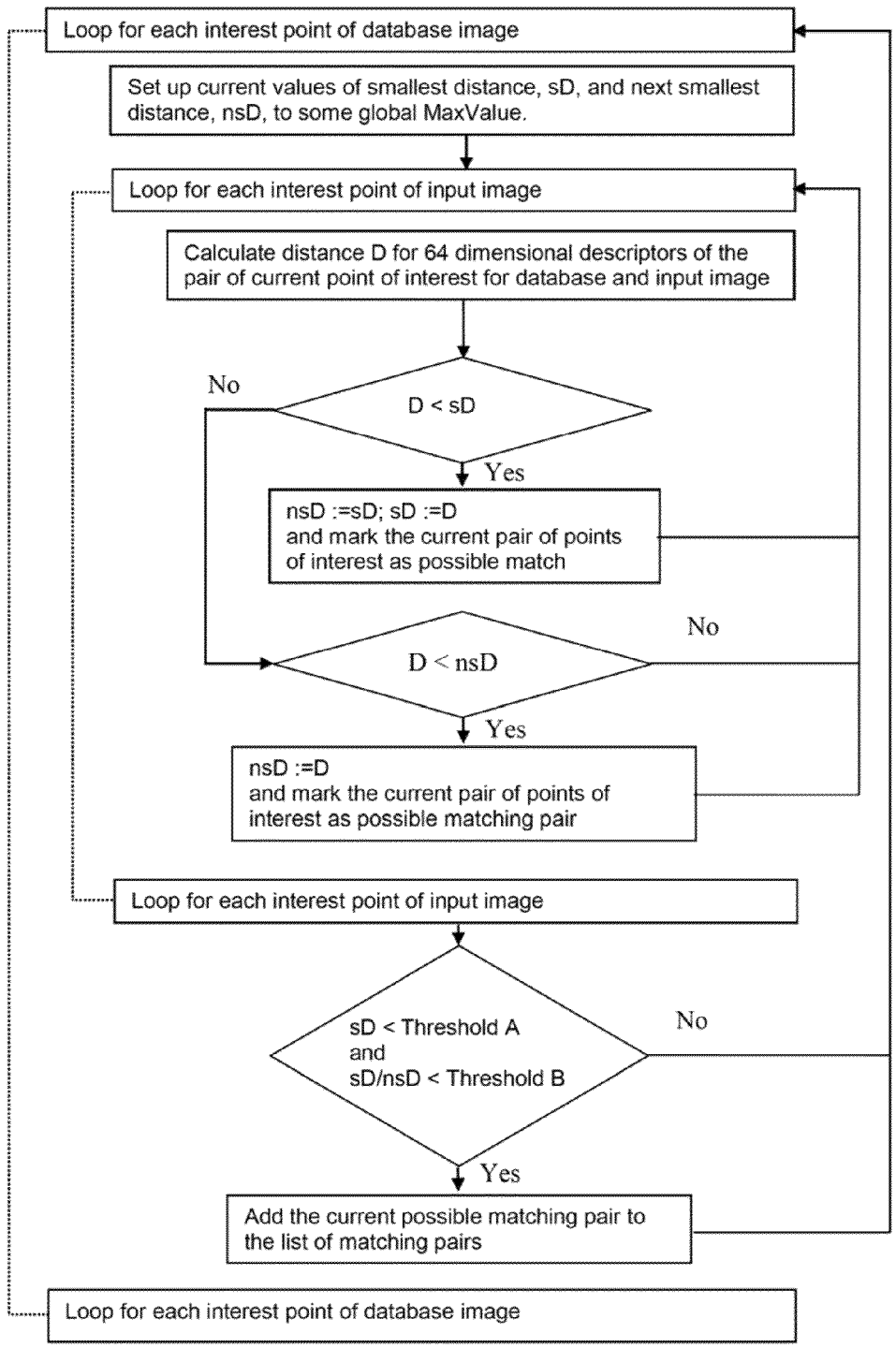
FIG. 5: Detailed diagram of the image descriptor matching part of the algorithm in the preferred embodiment of the invention.

Step-8: Performing an initial search of the matching descriptors among the stored database images from the database. FIG. 5 illustrates the implementation of a search for the matching pairs of the points of interest between the input image and a database image. The descriptor of the each point of interest from a tested input image is compared with all the descriptors from the database image.

For each pair of these descriptors the Euclidian distance between the 64-dimentional descriptor vectors is calculated. Among all the calculated distances the minimal distance and the distance which is smallest among all other calculated distances (i.e. next smallest distance) are retained.

The point of interest of the database image is selected as a matching point of interest for the point of interest of the tested image if:
i) the corresponding minimal distance of this pair is smaller than a certain adjustable threshold value, see Threshold A in FIG. 5, and
ii) the ratio between such minimal distance and the next smallest distance is smaller than an another adjustable threshold value, see Threshold B in FIG. 5.

Simultaneous application of these two conditions provides that 1) the selected pair of the points of interest matches the points of interest of the input and the database images with a similar local environment, and 2) that these local environments are substantially different from the local neighborhood of the other points of interest.

Step-9. The set of pairs of the points of interest obtained by aforementioned way for the input image and the database image is called a threshold-matched set of the points of interest. If, for the particular database image, the number of pairs of matched points of interest in the threshold-matched set is longer than a certain adjustable threshold number, then this database image is selected for the initial set of matching images.

Step-10: Deduction of the transformation matrixes which represents the transformation between the set of points of interest obtained as described in Step-4 for the input image to the paired points of interest selected for the threshold-matched sets, as described in Step 8, corresponding to database images in the initial matching set of the database images obtained in Step 9.

The choice of the type of the transformation matrix can be made upon the assumption about the type of possible geometrical transformation, such as affine, projective, etc. These transformations are insensitive to rotations, scaling, tilt, of image plane, etc. In the preferred embodiment of the invention, the transformation matrix is derived from two column matrixes of coordinates of the points of interest that are relevant to these images. Each of these column matrixes have X and Y coordinates of the point of interest as rows.

In the preferred embodiment of the invention, the Singular Value Decomposition method is used to evaluate a Moore-Penrose pseudo inverse matrix relevant to the column matrix of the points of interests coordinates in the input image. Accordingly, the transformation matrix is calculated as the matrix product of original column matrix for database image and Moore-Penrose pseudo inverse of column matrix for tested image.

Preferred embodiment of the invention implements the matrix of affine transformation which relates the points of interest coordinates for both aforementioned images. However, it is also possible for one skilled in the art to evaluate a more general projective transformation matrix or even more complex transformations by similar means.

Step-11: Deduction of the locations of the points of interest in the database image by applying the transformation matrix (obtained in Step-10) to the set of points of interest corresponded to the input image. The transformation matrix is applied to the original column matrix containing the coordinates of the input image points of interest to obtain a set of transformed coordinates for the points of interest in the input image.

Step-12: Comparison the transformed coordinates of the points of interest in the database image (obtained in Step-11) with the locations of the points of interest obtained by the SURF method for this image. Calculation of squares of Euclidian distances between the points of interest coordinates in the database image and transformed coordinates of the input image. This step is used to assess how well the deduced transformation matrix matches the paired points of interest, in other words, the input coordinates with applied transformation matrix are compared to the actual points of interest locations at the database image.

Step-13: The personal identification is performed based on a value of the cumulative matching criterion chi2. If the value of chi2 is below of a cumulative threshold value, the two images considered to be matched. Applying a cumulative predefined criterion chi2 to characterize and score the matching degree between the current and the database images (i.e. the vein patterns).

In the preferred embodiment of the invention, the adjustable cumulative threshold value for Chi2 for a pair of two images is evaluated as a mean square distance between the coordinates of the points of interest of database image and transformed coordinates of input image.

The tested image with the smallest Chi2 value is selected as a Best Matching Image for the input image.

Image Analysis:

Step-14: Deriving probabilities (i.e. rates) of a true and a false positive matching from the obtained values of Chi2 for the total number of compared and matched images.

The algorithm disclosed in Steps 1-14 indicate that the false positive rate of the matching is less than 0.001%, which is in a good agreement with the results have been reported for alternative well-known biometric authentication methods.

Figure 4:
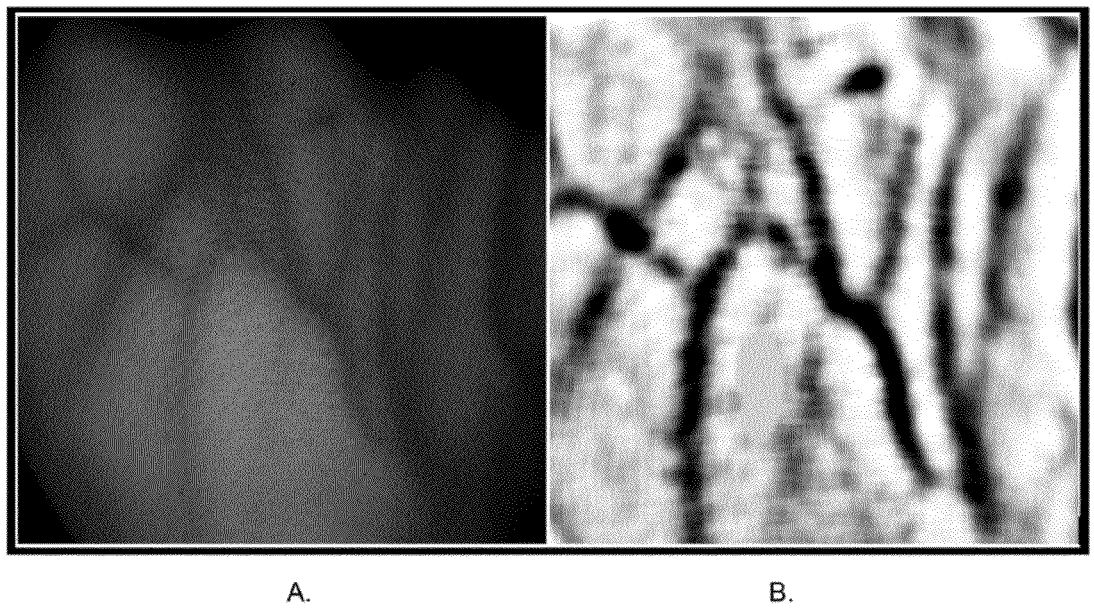
FIG. 4: Applying a high-pass, low-pass filters and contrast enhancement to the image. Original (4A) and processed (4B) images of the human hand veins pattern are shown.

FIG. 4 shows the example of a high- and low-frequency-pass filtering application to the image, in combination with the contrast enhancement, used to obtain the of human hand veins patterns (Steps-2, 3 of the aforementioned routine) as a preprocessing required for the matching analysis. The original image (FIG. 4A) and the processed (FIG. 4B) image are shown.

FIG. 5 shows the image descriptor matching part of the algorithm (see FIG. 3, Steps-7-8) more in detail, including comparing the sets of points of interest for the database image and the input images, and selecting the pairs of possible matching points of interest.

While in the preferred embodiment of the invention the gray-scale (intensity) images of the human hand vein-pattern is used, other embodiments could use foil color images for the same purposes.

It is obvious to the skilled in the art, that most of the image processing procedures are dependent on a number of adjustable parameters, such as settings of averaging windows for high-pass and low-pass filters, percentage of pixels with outlying intensity values removed during image contrast enhancement, settings of the SURF procedure, as well as multiple threshold values relevant to image comparison procedures.

In the preferred embodiment of the device, a generic procedure, which is using a set of test images to simultaneously optimize the values of these adjustable parameters, is implemented. This procedure establishes a target image matching matrix which contains a zero values for the elements representing non matching images and some values for the pairs of matching images. The procedure starts from a pre-defined set of adjustable parameters and performs all routine shown in the FIG. 3 for any set of images from the database.

Moreover, the procedure establishes penalty values for each occurrence of incorrect match or absence of a correct match, further collecting these penalty values in an aggregated target function value. The procedure employs non-gradient Nedler-Mead simplex search in the space of adjustable parameters to minimize the target function value and to establish a set mutually optimized parameters for our image processing and image comparison procedures.

Figure 6:
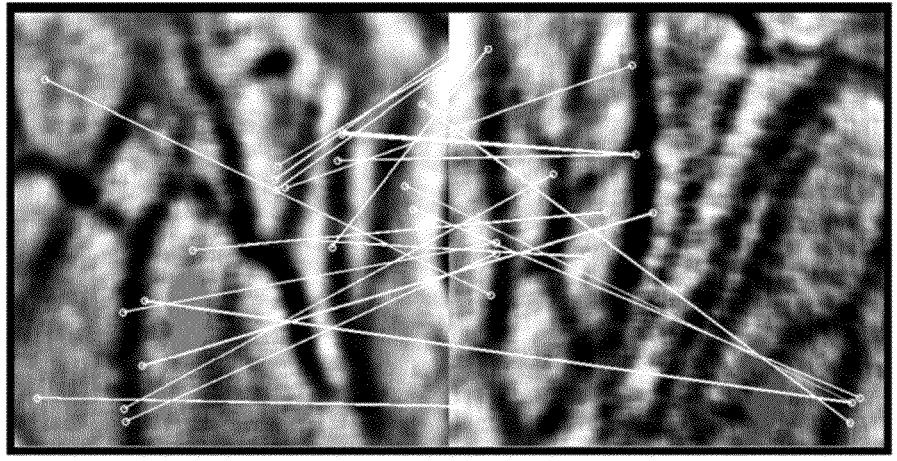
FIG. 6: Illustration of the matching procedure of the algorithm for two different images that taken for the same person at different time.
Figure 6:
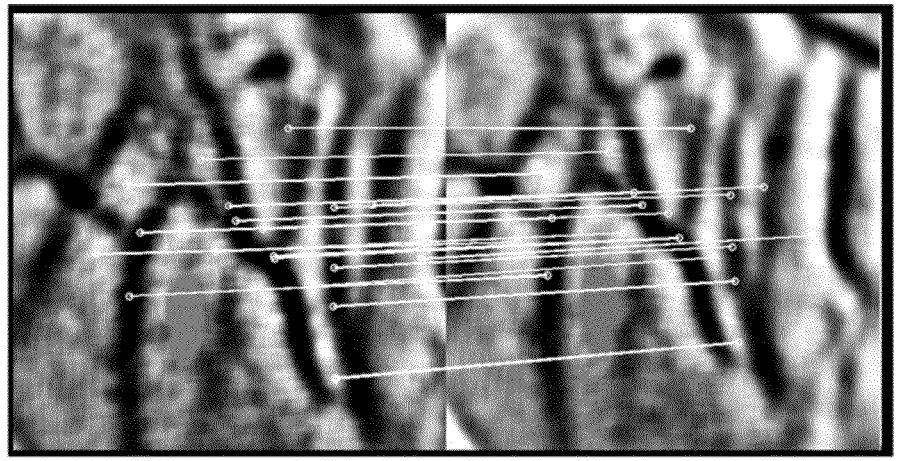

FIG. 6 illustrated the actual performance of the matching procedure of the algorithm, (see the Step-12). The points of interest for two different images are taken for the same person at different times. FIG. 6A illustrates a good match with, a chi2 cumulative criterion having value of 30, while FIG. 6B illustrates a bad match with a cumulative criterion chi2 having value in the range of 2000-10000. This demonstrates a good efficiency of the matching procedure.

Figure 7:
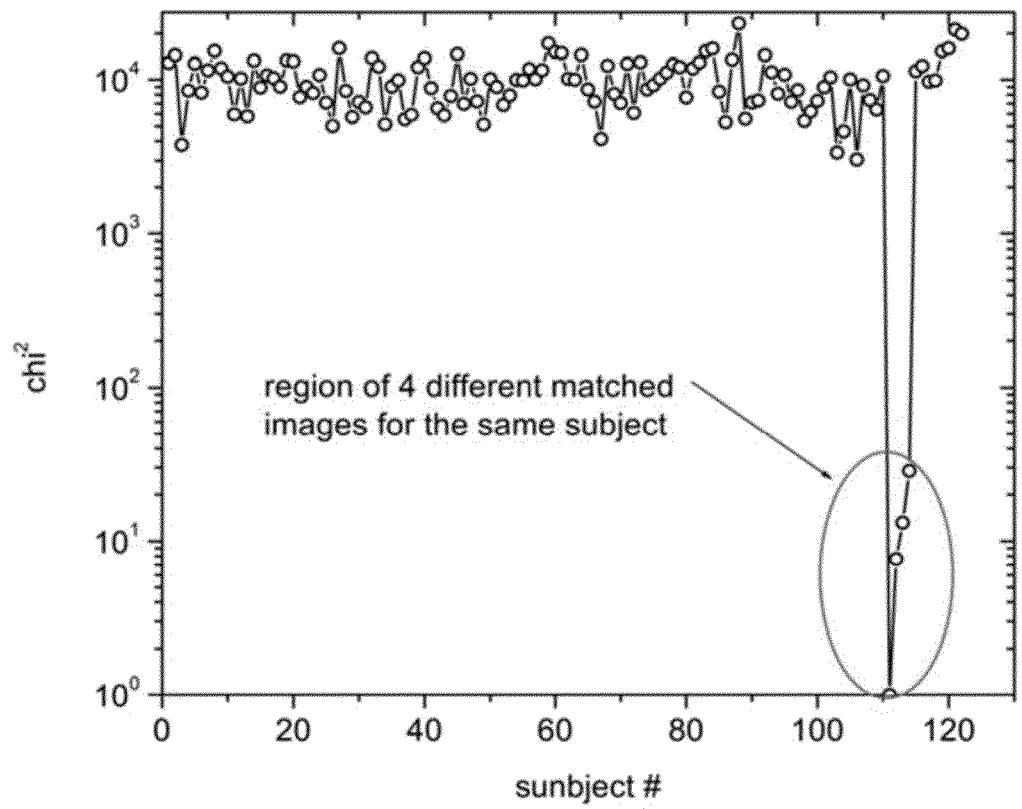
FIG. 7: Algorithm implementation example. A matching criterion values for the comparison between an acquired image and multiple images from a database is shown. The ellipse marks the region where all 4 images are matched for the same individual.

FIG. 7 shows a comparison between a single image against multiple database images. The ellipse marks the region where all four images of the same subjects are matched which demonstrates high sensitivity of image matching procedure.

Although several exemplary embodiments have been herein shown and described, those of skill in the art will recognize that many modifications and variations are possible without departing from the spirit and scope of the invention, and it is intended to measure the invention only by the appended claims.

We claim:

1. A portable device for identification of an individual based on a vein-pattern comprising:
    a smartphone;
    a camera built in the smartphone, the camera acquiring an input image of a skin area with the vein-pattern of the individual, the input image is acquired in the near infrared (NIR) spectrum of light radiation;

a built-in smartphone central processor unit (CPU) performs processing of the acquired input image to extract an input vein-pattern image from the obtained image of the skin area;

the CPU performs deduction of points of interest from the vein-pattern image and calculation of their coordinates;

the CPU also creates a 64-dimensional descriptor vector for each of the point of interest, the 64-dimensional descriptor vector including information about features of a local image around the each respective point of interest;

the CPU compares the obtained image descriptor vector with each descriptor vector from a database of descriptor vectors; the database is stored in the smartphone;

the CPU uses a criterion of minimum Euclidian distance between descriptor vectors and a criterion of sufficient separation between minimum Euclidian distances to establish pairs of matching points of interest for two images: the input image and each image stored in the database, and assuring the individual identification if the number of pairs of matched points of interest is greater than a predefined threshold.

2. The device of claim 1, further comprising additional processing in the CPU to improve an accuracy of the identification, the additional processing comprising:

calculating coordinates of the matched pairs of points of interest of input and database image;

calculating a transformation matrix using the coordinates of the matched pairs;

the transformation matrix reflecting a geometrical transformation of the coordinates of the input image into coordinates of a selected database image; the selected database image is one that was selected after the vectors comparison and for which the number of pairs of the matched points of interest is greater than the predefined threshold;

calculating transformed coordinates of the points of interest of the input image;

comparing the transformed coordinates with initial coordinates; and determining an improved individual identification if a distance between the initial and the transformed coordinates is less than a cumulative threshold.

3. The device of claim 2, wherein the cumulative threshold is determined as a mean square distance between the initial and the transformed coordinates.

4. The device of claim 2, wherein the transformation matrix is an affine, projective transformation.

5. The device of claim 2, wherein the transformation matrix is a general class of image transformations.

6. The device of claim 1, wherein the coordinates of the points of interest and 64-dimentional descriptor vectors are calculated using a Speeded-Up Robust Features (SURF) method.

7. The device of claim 1, wherein the database is transmitted to the smartphone via a 3G or 4G technology, Bluetooth, or Wi-Fi, and the database is stored in the smartphone memory.

8. The device of claim 1, further comprising a switch, performing switching of the camera operation between a visible and the NIR spectrum.

9. The device of claim 8, wherein the camera has an auto-focus feature operating in both the visible and the NIR spectrum.

10. The device of claim 9, further comprising a lighting feature is provided by the device to improve the quality of the image both in the visible and the NIR light spectrum.

11. The device of claim 1, further comprising a wireless communication of the smartphone with a remote server; the smartphone having an option to choose the server for the image processing, a storage of the database and a command to send results of the individual identification back to the smartphone for display.

12. The device of claim 1, wherein the scale vein-pattern image is a gray scale image extracted based on a spatial low frequency and a high frequency filtering and image contrast enhancement.

13. The device of claim 1, being used for collecting personal biometric information.

14. The device of claim 1, being used for accessing individual specific information for the identified individual.

15. The device of claim 1, being used for allowing an access to the information or site.

16. The device of claim 1, being used for performing tasks related with personnel and population surveying and management.

17. The device of claim 1, wherein the number of matching pairs of points of interest signifying possible identification of an input image is adjustable.

18. The device of claim 1, wherein the threshold value of minimum Euclidian distance between 64-dimentional descriptor vectors of two points of interest is adjustable.

19. The device of claim 1, wherein the threshold value of a ratio between the minimum Euclidian distances for two pairs of matching points of interest is adjustable.

20. The device of claim 1, wherein the coordinates of the points of interest and 64-dimentional descriptor vectors are calculated using a Speeded-Up Robust Features (SURF) method, and a value of a hessian threshold is adjustable.

* * * * *